(12) United States Patent
Van Der Linden

(10) Patent No.: US 10,328,194 B2
(45) Date of Patent: Jun. 25, 2019

(54) ARRANGEMENT FOR CARDIOPULMONARY BYPASS, AND A METHOD FOR CARDIOPULMONARY BYPASS

(71) Applicant: CARDIA INNOVATION AB, Kungens Kurva (SE)

(72) Inventor: Jan Van Der Linden, Saltsjöbaden (SE)

(73) Assignee: CARDIA INNOVATION AB, Kungens Kurva (SE)

( * ) Notice: Subject to any disclaimer, the term of this patent is extended or adjusted under 35 U.S.C. 154(b) by 282 days.

(21) Appl. No.: 15/522,008

(22) PCT Filed: Oct. 15, 2015

(86) PCT No.: PCT/EP2015/073890
§ 371 (c)(1),
(2) Date: Apr. 26, 2017

(87) PCT Pub. No.: WO2016/066433
PCT Pub. Date: May 6, 2016

(65) Prior Publication Data
US 2017/0326289 A1    Nov. 16, 2017

(30) Foreign Application Priority Data
Oct. 29, 2014   (EP) .................................. 14190791

(51) Int. Cl.
*A61M 1/36*      (2006.01)
*A61M 1/16*      (2006.01)

(52) U.S. Cl.
CPC ........ *A61M 1/3627* (2013.01); *A61M 1/3666* (2013.01); *A61M 1/1698* (2013.01); *A61M 2202/0208* (2013.01); *A61M 2202/0225* (2013.01); *A61M 2202/0266* (2013.01)

(58) Field of Classification Search
CPC .. A61M 1/3627; A61M 1/3629; A61M 1/363; A61M 1/3632; A61M 1/3633; A61M 1/3635; A61M 1/3636; A61M 1/3666; A61M 1/3667; A61M 1/1698; A61M 2202/0208; A61M 2202/0225; A61M 2202/0266
See application file for complete search history.

(56) References Cited

U.S. PATENT DOCUMENTS

| | | | |
|---|---|---|---|
| 5,725,492 A * | 3/1998 | Igo | A61M 1/1698 604/23 |
| 6,770,048 B2 | 8/2004 | Fini | |
| 6,994,685 B2 | 2/2006 | Van Der Linden | |
| 7,549,973 B2 | 6/2009 | Van Der Linden et al. | |

* cited by examiner

*Primary Examiner* — Philip R Wiest
(74) *Attorney, Agent, or Firm* — Greer, Burns & Crain, Ltd.

(57) ABSTRACT

An arrangement and a method for cardiopulmonary bypass is provided. The arrangement includes a reservoir configured to receive blood from the cardiotomy of a patient. An oxygenator receives the blood from the reservoir. An arterial connection is connected to the patient for supplying the blood from the oxygenator. A pump is provided for pumping the blood through the oxygenator to the arterial connection and the patient. The arrangement includes a supply device including a supply conduit attached to the reservoir. The supply device supplies a displacing gas to the reservoir via the supply conduit.

17 Claims, 4 Drawing Sheets

ARRANGEMENT FOR CARDIOPULMONARY BYPASS, AND A METHOD FOR CARDIOPULMONARY BYPASS

BACKGROUND

The present invention refers to an arrangement for cardiopulmonary bypass according to the preamble of claim 1. The invention also refers to a method for cardiopulmonary bypass according to the preamble of claim 13.

Arrangements for cardiopulmonary bypass are frequently used in cardiothoracic surgery, especially in open heart surgery. A cardiotomy reservoir may be included in the arrangement for receiving blood entering the open operation wound, the open cardiotomy, during the surgery.

U.S. Pat. No. 6,770,048 discloses a combined device for cardiopulmonary bypass. The device comprises a venous blood reservoir and cardiotomy reservoir in an extracorporeal circuit, which may comprise a pump and an oxygenator.

Together with the blood from the operation wound, i.e. the open cardiotomy, gases, including carbon dioxide, may be sucked to the cardiotomy reservoir. If carbon dioxide is collected in the cardiotomy reservoir, the gas will be in contact with the blood. Since carbon dioxide dissolves easily in blood, there is a risk for increased levels of carbon dioxide in the blood.

It is also advantageous to add carbon dioxide to the operation wound, as is described in EP-1239915 and EP-1494606. The carbon dioxide will create a protective layer above the open cardiotomy. However, with such a supply of carbon dioxide, the problem of solution of carbon dioxide in the blood in the cardiotomy reservoir is further increased.

This problem may be at least partly remedied by increasing the flow of air or oxygen through the oxygenator, thereby increasing the amount of carbon dioxide being removed from the blood. The amount of carbon dioxide that can be removed by this measure is however limited.

SUMMARY

The object of the present invention is to overcome the problem discussed above and to reduce the carbon dioxide content in the blood of a reservoir, such as the venous and/or cardiotomy reservoir, during cardiopulmonary bypass. More precisely, it is aimed at a reduction or elimination of the influence of carbon dioxide gas that has been supplied to the venous and/or cardiotomy reservoir from the open surgical wound via a suction pump when the surgical wound is being insufflated with carbon dioxide.

This object is achieved by the arrangement initially defined, which is characterized in that the arrangement comprises a supply device including a supply conduit attached to the reservoir and that the supply device is configured to supply a displacing gas to the reservoir via the supply conduit to force away gas already present in the reservoir.

The supply of the displacing gas to the reservoir contributes to remove or force away gases already present in the reservoir, such as the cardiotomy reservoir. In particular, the supply of the displacing gas contributes to force away or displace carbon dioxide present in the reservoir. Uptake of carbon dioxide gas into the blood in the reservoir is thus reduced or prevented, so that the carbon dioxide concentration of the blood received by the oxygenator is reduced.

Thus the normal carbon dioxide content in the venous and arterial blood will not, or only marginally, be influenced by insufflation of carbon dioxide gas in the open surgical wound.

The displacing gas may be any suitable gas, such as an oxygen-containing gas, for instance air, nitrogen, etc.

According to an embodiment of the invention, the arrangement comprises at least one cardiotomy conduit including a pump to permit blood from the open cardiotomy to be sucked to the reservoir. During such sucking, also gases, containing for example carbon dioxide, present in the cardiotomy will be conveyed together with the blood from the open cardiotomy to the reservoir. The invention thus prevents these gases, especially carbon dioxide, from being solved in the blood received in the reservoir.

According to a further embodiment of the invention, the reservoir encloses an inner space having a lower part, configured to receive the blood from the cardiotomy, and an upper part, configured to receive gas from the cardiotomy, wherein the supply device is configured to supply the displacing gas to the reservoir to force away said gas already present in the upper part.

According to a further embodiment of the invention, the reservoir comprises an outlet opening permitting the upper part of the inner space of the reservoir to communicate with the surrounding atmosphere to release said gas already present from the upper part. By the supply of the displacing gas, the carbon dioxide will thus be displaced and forced out through outlet opening.

According to a further embodiment of the invention, the supply conduit comprises an outlet member provided in the inner space of the reservoir.

According to a further embodiment of the invention, the outlet member is provided in the upper part of the inner space.

According to a further embodiment of the invention, the outlet member comprises a diffusing member configured to supply the displacing gas in a laminar flow in the upper part of the inner space of the reservoir.

According to a further embodiment of the invention, wherein the outlet member extends into the lower part of the inner space.

According to a further embodiment of the invention, the outlet member is perforated permitting the displacing gas to enter said blood in the lower part of the reservoir. For instance, the outlet member may comprise a perforated hose or pipe.

According to a further embodiment of the invention, the supply conduit comprises a filter for filtering the displacing gas before entering the reservoir.

According to a further embodiment of the invention, the filter is provided in the upper part of the inner space. In particular, the filter may be comprised by the outlet member.

According to a further embodiment of the invention, the supply conduit comprises a control valve configured to permit control of the flow of the displacing gas to the reservoir.

According to a further embodiment of the invention, the control valve is configured to adjust the flow of the displacing gas to be between 0 and 5 liter per minute.

According to a further embodiment of the invention, the arrangement comprises an arterial filter provided downstream the oxygenator and configured to filter the blood from the oxygenator.

According to a further embodiment of the invention, the supply device comprises a humidifying device configured to humidify the displacing gas supplied to the reservoir via the supplied conduit.

According to a further embodiment of the invention, the arrangement comprises a venous connection configured to be connected to venous blood of a patient.

According to a further embodiment of the invention, the reservoir is connected to the venous connection and configured to receive the blood from the venous connection, According to this embodiment, the reservoir may be a common reservoir receiving both the venous blood and the blood from the cardiotomy.

According to a further embodiment of the invention, the reservoir comprises a cardiotomy reservoir, wherein the arrangement comprises a venous reservoir connected to the venous connection and configured to receive the blood from the venous connection. The arrangement is configured to supply the blood received in the venous reservoir to the oxygenator.

According to this embodiment, two separate reservoirs are provided, one cardiotomy reservoir receiving blood from the cardiotomy and one venous reservoir receiving venous blood.

According to a further embodiment of the invention, the venous reservoir and the cardiotomy reservoir are included in a common container. Advantageously, the cardiotomy reservoir may have an outlet located in the venous reservoir to permit blood received in the cardiotomy reservoir to be supplied to the venous reservoir to be mixed with the venous blood before being supplied to the oxygenator.

According to a further embodiment of the invention, the arrangement comprises a further supply device configured to supply carbon dioxide to the cardiotomy of the patient.

According to a further embodiment of the invention, the further supply device comprises a carbon dioxide source and a supply hose comprising an outlet to be provided in the open cardiotomy.

The outlet may comprise an outlet nozzle, which advantageously may include a porous body configured to be positioned in the open cardiotomy. The porous body may be arranged to supply the carbon dioxide to the open cardiotomy in a controlled flow in order to enable the formation of a carbon dioxide cushion intended to fill substantially the open cardiotomy and prevent air from the surrounding atmosphere from reaching the open cardiotomy. The porous body may be manufactured in foam rubber material.

The object is also achieved by the method initially defined which is characterized by the step of: supplying displacing gas to the reservoir.

According to a development of the invention, the method comprises the step of: supplying the displacing gas to an inner space of the reservoir to force away gas already present in an upper part of the inner space, wherein the blood from the cardiotomy is received in a lower part of the inner space of the reservoir.

According to a further development of the invention, the method comprises the step of: releasing said gas already present from the upper part of the inner space of the reservoir through an outlet opening permitting the upper part of the inner space of the reservoir to communicate with the surrounding atmosphere.

According to a further development of the invention, the method comprises the step of: supplying the displacing gas in a laminar flow in the upper part of the inner space of the reservoir.

According to a further development of the invention, the method comprises the step of: controlling the flow of the displacing gas to the reservoir.

According to a further development of the invention, the method comprises the step of: filtering the blood from the oxygenator According to a further development of the invention, the method comprises the step of: humidifying the displacing gas to be supplied to the reservoir.

According to a further development of the invention, the method comprises the step of: conveying venous blood of a patient to the reservoir, wherein the venous blood and the blood from the cardiotomy is received in the reservoir and supplied to the oxygenator.

According to a further development of the invention, the method comprises the steps of: providing a venous reservoir and a cardiotomy reservoir, conveying venous blood from a patient to a venous reservoir, conveying the blood from the cardiotomy of the patient to the cardiotomy reservoir, and supplying the venous blood received in the venous reservoir and the blood received in the cardiotomy reservoir to the oxygenator.

According to a further development of the invention, the method comprises the step of: conveying the blood from the cardiotomy reservoir to the venous reservoir to permit the venous blood and the blood from the cardiotomy to be mixed before being supplied to the oxygenator.

BRIEF DESCRIPTION OF THE DRAWINGS

The present invention is now to be explained more closely through a description of various embodiments and with reference to the drawings attached hereto.

DETAILED DESCRIPTION

Figure 1:
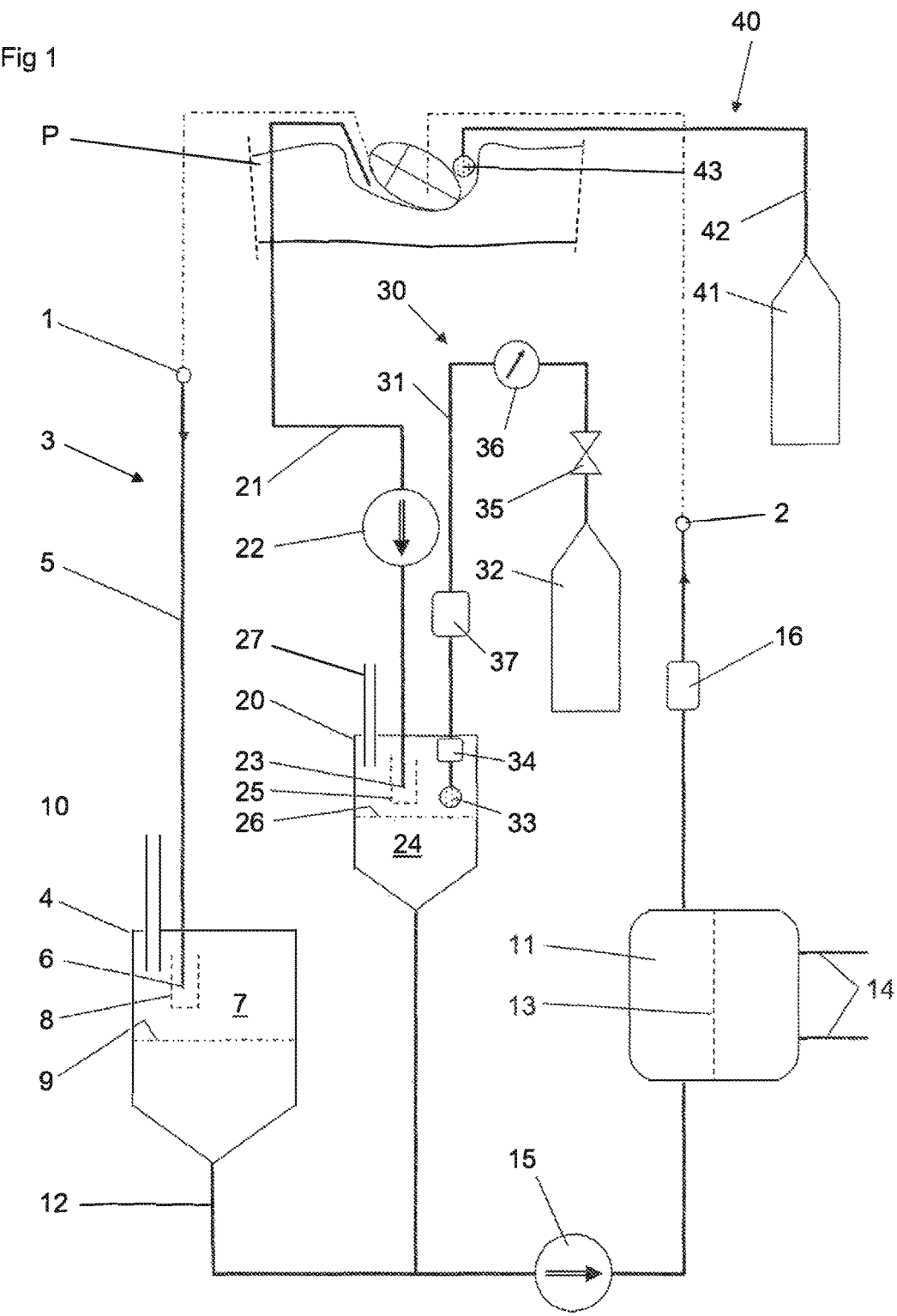
FIG. 1 discloses schematically a representation of an arrangement for cardiopulmonary bypass according to a first embodiment of the invention.

FIG. 1 discloses a first embodiment of an arrangement for cardiopulmonary bypass. The arrangement comprises a venous connection 1, an arterial connection 2 and a circuit 3 extending from the venous connection 1 to the arterial connection 2.

The venous connection 1 is configured to be connected to venous blood of a patient P schematically indicated. The blood is thus conveyed from the patient via the venous connection 1 through the circuit 3 and to the arterial connection 2. The arterial connection 2 is configured to be connected to the patient P for supplying the blood back to the arterial side of the cardiovascular system of the patient P.

The arrangement also comprises a reservoir comprising or being a venous reservoir 4, which is connected to the venous connection 1 and included in the circuit 3. The venous reservoir 4 is configured to receive the blood venous side of the cardiovascular system of the patient P via the venous connection 1.

The circuit 3 comprises a venous line 5 extending from the venous connection 1 to an outlet end 6 provided in an upper part of an inner space 7 of the venous reservoir 4.

A filtering and defoaming element 8 is provided at the outlet end 6. The blood conveyed to the venous reservoir 4 passes through the filtering and defoaming element 8 before reaching a lower part of the inner space 7.

The blood level 9 determines the transition from the lower part and the upper part of the inner space 7. The blood level 9 may vary.

The venous reservoir 4 may also comprise an outlet opening 10 communicating with the surrounding atmosphere.

Also included in the circuit 3 is an oxygenator 11, which is configured to receive the blood from the venous reservoir 4 via an arterial line 12 of the circuit 3. The oxygenator 11 comprises in a known manner a membrane 13 through which carbon dioxide may pass from the blood to an external circuit 14 and through which oxygen may pass from the external circuit 14 to the blood.

Furthermore, the circuit 3 includes a pump 15, which is provided on the arterial line 12 and configured to pump the blood through the circuit 3 and oxygenator 11.

In the embodiments disclosed, the pump 15 is provided upstream the oxygenator 11. It should be noted, that the pump 15 may as well be provided downstream the oxygenator 11.

The pump 15 may comprise any kind of suitable pumps, such as a roller pump, a centrifugal pump, etc.

An arterial filter 16 may also be included in the circuit 3 and provided on the arterial line 12. The arterial filter 16 is provided downstream the oxygenator 11 and the pump 15, and upstream, or immediately upstream the arterial connection 2. Filtering of the blood to be delivered back to the cardiovascular system of the patient P may thus be ensured.

Furthermore, the arrangement comprises a reservoir comprising or being a cardiotomy reservoir 20. The cardiotomy reservoir 20 is configured to receive blood from the open cardiotomy of the patient P as indicated in FIG. 1.

In the first embodiment, the venous reservoir 4 and the cardiotomy reservoir 20 are separate from each other.

A cardiotomy conduit 21 extends from the open cardiotomy of the patient P to the cardiotomy reservoir 20. A pump 22 is provided on the cardiotomy conduit 21 permit blood from the open cardiotomy to be sucked to the cardiotomy reservoir 20 through the cardiotomy conduit 21.

An outlet end 23 of the cardiotomy conduit 21 is provided in an upper part of an inner space 24 of the cardiotomy reservoir 20.

A filtering and defoaming element 25 is provided at the outlet end 23 of the cardiotomy conduit 21. The blood conveyed to the cardiotomy reservoir 20 passes through the filtering and defoaming element 25 before reaching a lower part of the inner space 24.

The blood level 26 determines the transition between the lower part and the upper part of the inner space 24. The blood level 26 may vary.

The cardiotomy reservoir 20 may also comprise an outlet opening 27 communicating with the surrounding atmosphere.

The arrangement also comprises a supply device 30 including a supply conduit 31 extending to the cardiotomy reservoir 24. The supply device 30 is configured to supply a displacing gas to the cardiotomy reservoir 24 via the supply conduit 31. The displacing gas may be any suitable gas, such as an oxygen-containing gas, for instance air, nitrogen, etc.

The supply conduit 31 is connected to a source 32 containing the displacing gas, for instance air. The source 32 may be pressurized. Alternatively, the displacing gas may be supplied by means of a pump provided on the supply conduit 31.

The supply device 30 is configured to supply the displacing gas to the upper part of the inner space 24 to force away gas already present in the upper part of the inner space 24.

The supply conduit 31 comprises an outlet member 33 provided in the upper part of the inner space 24. The displacing gas will thus be introduced into the upper part of the inner space 24.

Furthermore, the supply conduit 31 comprises a filter 34 for filtering the displacing gas before the gas enters the cardiotomy reservoir 20.

The supply device 30 may also comprise a control valve 35 provided on the supply conduit 31 and configured to permit control of the flow of the displacing gas to the cardiotomy reservoir 20. Moreover a flow meter 36 may be provided on the supply conduit 31 to indicate the flow of the displacing gas. The flow may amount to 0-5 liter per minute, or preferably 0.2-4 liter per minute.

The supply device 30 may also comprise a humidifying device 37, which may be provided on the supply conduit 31. The humidifying device 37 is configured to humidify the displacing gas supplied to the cardiotomy reserevoir 20 via the supply conduit 31.

The arrangement may also comprise a further supply device 40 configured to supply carbon dioxide to the cardiotomy of the patient P. The further supply device 40 comprises a carbon dioxide source 41 and a supply hose 42 comprising an outlet to be positioned in the open cardiotomy for the supply of carbon dioxide.

In the embodiments disclosed the outlet comprises an outlet nozzle 43 configured to be positioned in the open cardiotomy of the patient P. The outlet nozzle 43 may comprise a porous body The porous body may be arranged to supply the carbon dioxide to the open cardiotomy in a controlled flow in order to enable the formation of a carbon dioxide cushion intended to fill substantially the open cardiotomy and prevent air from the surrounding atmosphere from reaching the open cardiotomy. The porous body may be manufactured in foam rubber material.

During the sucking of blood through the cardiotomy conduit 21, also gases, containing carbon dioxide, present in the cardiotomy will be conveyed together with the blood from the open cardiotomy to the cardiotomy reservoir 20. By supplying the displacing gas to the cardiotomy reservoir 20, the carbon dioxide present therein is prevented from being solved in the blood received in the cardiotomy reservoir 20.

Figure 2:
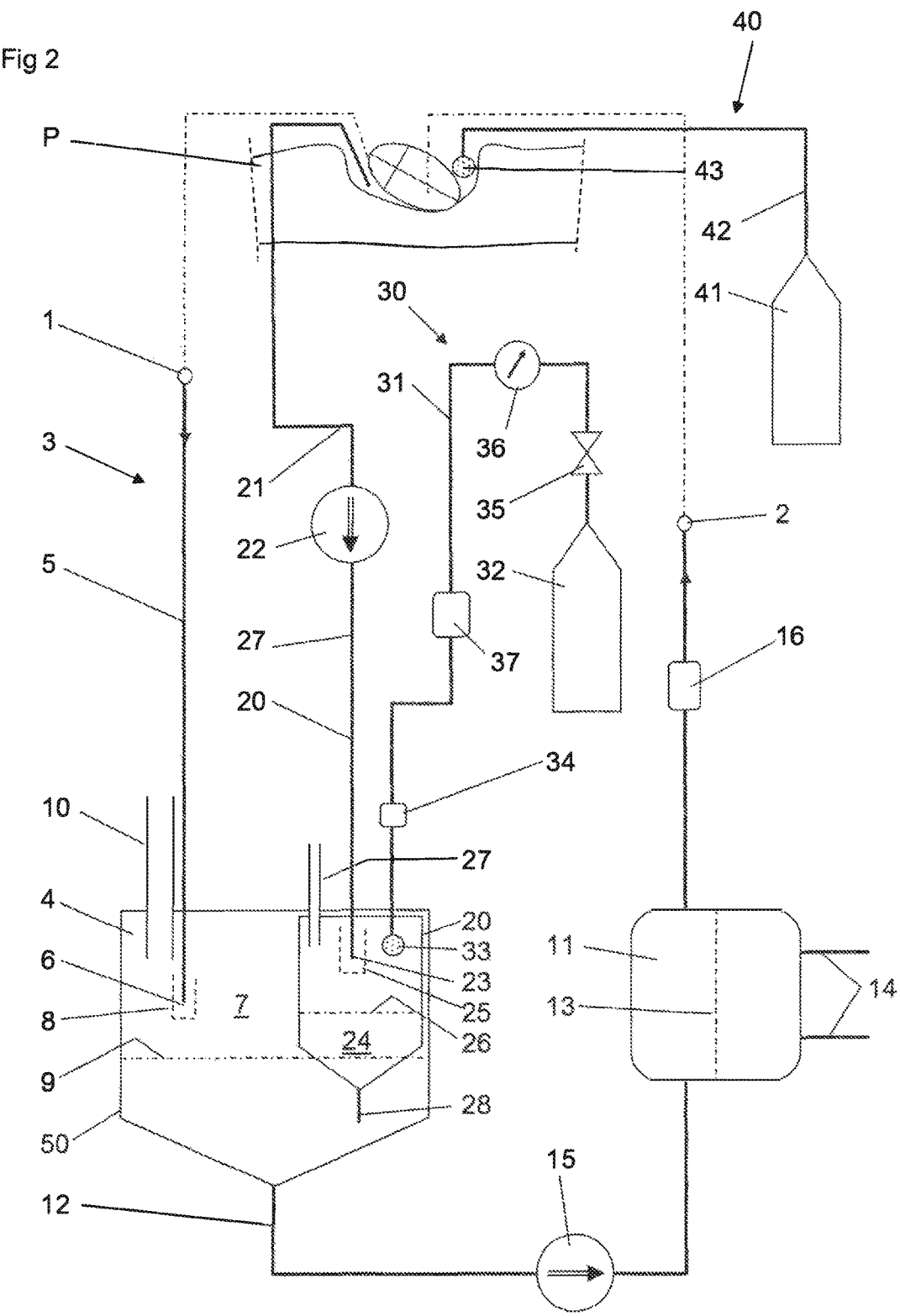
FIG. 2 discloses schematically a representation of an arrangement for cardiopulmonary bypass according to a second embodiment of the invention.

FIG. 2 discloses a second embodiment of the arrangement for cardiopulmonary bypass, which differs from the first embodiment in that the cardiotomy reservoir 20 and the venous reservoir 4 are provided in a common container 50. More precisely, the cardiotomy reservoir 20 is provided in the venous reservoir 4 as can be seen in FIG. 2. Thus the venous reservoir 4 forms the common container 50. It should be noted that the same reference signs have been used in all embodiments for elements having the same or a similar function.

The cardiotomy reservoir 20 has an outlet 28 which is located in the inner space 7 of the venous reservoir 4. The blood received in the cardiotomy reservoir 20 will thus be supplied to the venous reservoir 4, and mixed with the venous blood therein.

Figure 3:
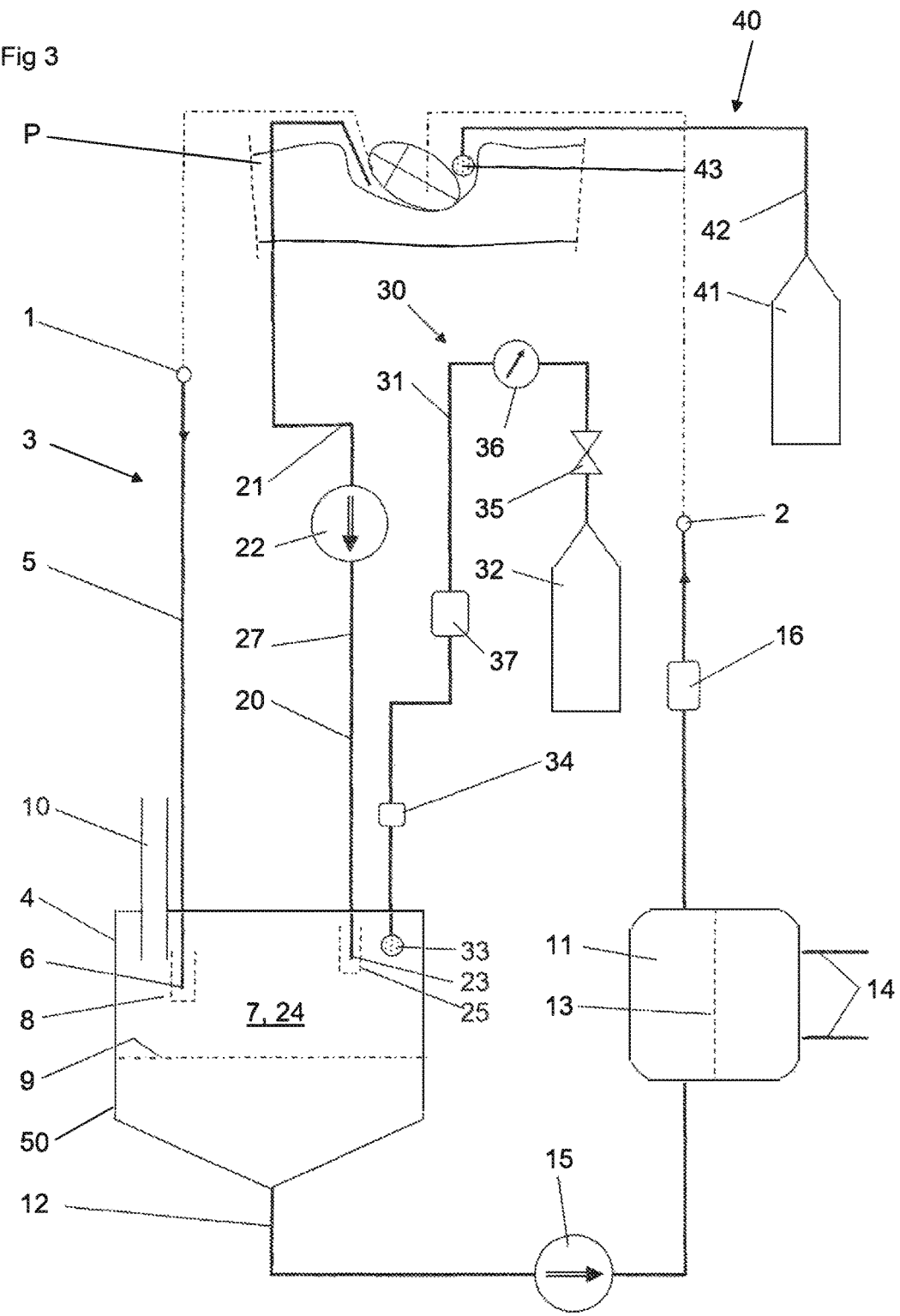
FIG. 3 discloses schematically a representation of an arrangement for cardiopulmonary bypass according to a third embodiment of the invention.

FIG. 3 discloses a third embodiment of the arrangement for cardiopulmonary bypass, which differs from the second embodiment in that no separate cardiotomy reservoir is provided.

In the third embodiment, the reservoir 4 forms both the venous reservoir and the cardiotomy reservoir. The reservoir 4 comprises a common container 50 and is configured to receive the venous blood via the venous connection and the blood from the cardiotomy via the cardiotomy conduit 21.

The cardiotomy conduit 21 has its outlet end 23 located in the inner space 7 of the reservoir 4. Also the outlet member 33 of the supply device 30 is provided in the inner space 7 of the reservoir 4.

Figure 4:
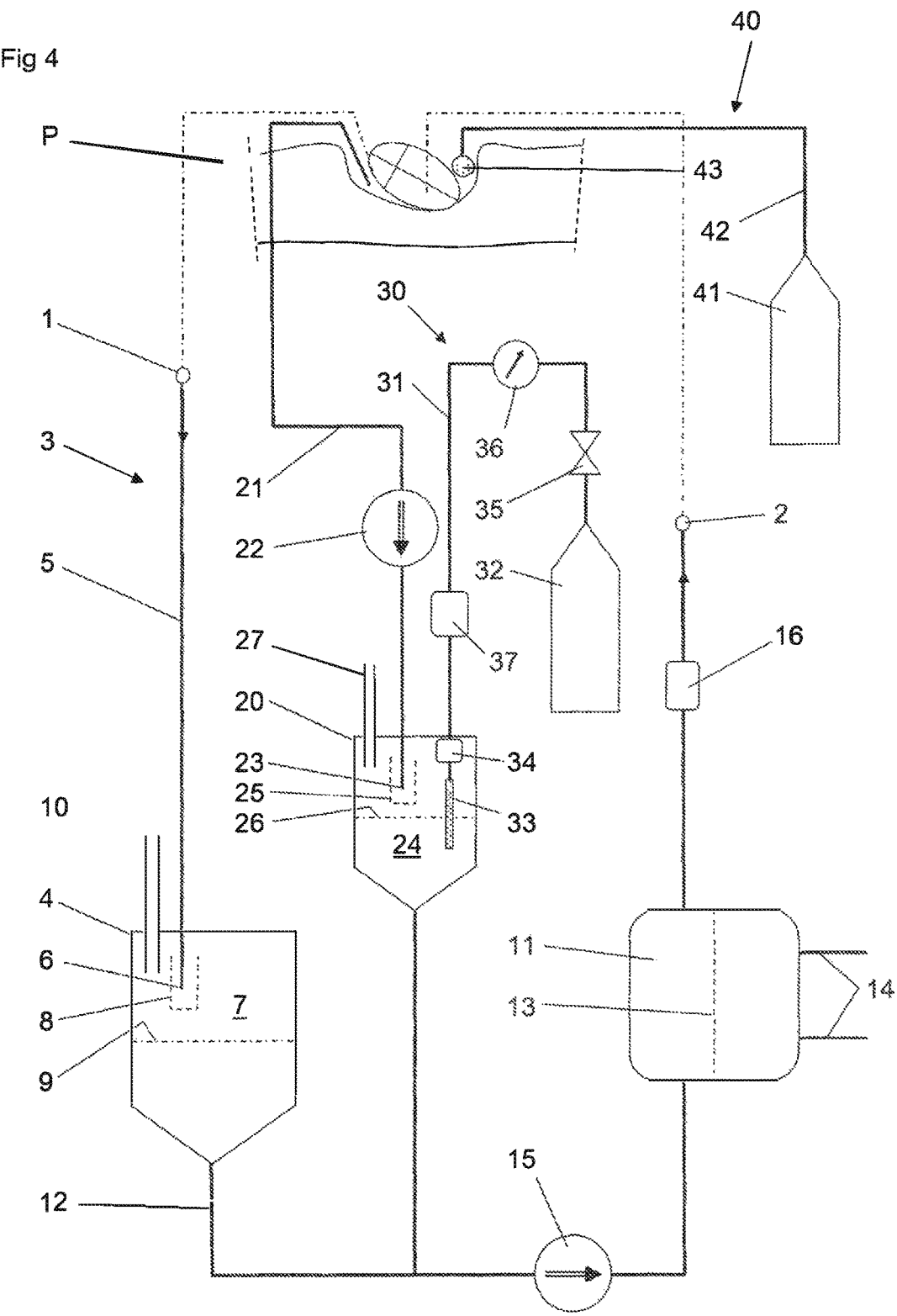
FIG. 4 discloses schematically a representation of an arrangement for cardiopulmonary bypass according to a fourth embodiment of the invention.

FIG. 4 discloses a fourth embodiment of the arrangement for cardiopulmonary bypass, which differs from the first embodiment in that the outlet member 33 is perforated and extends into the blood in the lower part of the inner space 24. The outlet member 33 may comprise a perforated pipe or hose permitting the displacing gas to enter the blood in the lower part of the inner space 24. A part of the perforated outlet member 33 may be located in the upper part of the inner space 24 as can be seen in FIG. 4.

A fifth embodiment differs from the second embodiment only in that the outlet member is replaced by the perforated outlet member 33 of the fourth embodiment shown in FIG. 4.

A sixth embodiment differs from the third embodiment only in that the outlet member is replaced by the perforated outlet member 33 of the fourth embodiment or fifth embodiment shown in FIG. 4.

The present invention is not limited to the embodiments disclosed, but may be varied and modified within the scope of the following claims.

The invention claimed is:

1. An arrangement for cardiopulmonary bypass, comprising:
   a reservoir configured to receive blood from the cardiotomy of a patient;
   an oxygenator configured to receive the blood from the reservoir;
   an arterial connection configured to be connected to the patient for supplying the blood from the oxygenator;
   a pump for pumping the blood through the oxygenator to the arterial connection and the patient; and
   a supply device including a supply conduit attached to the reservoir and the supply device is configured to supply a displacing gas to the reservoir via the supply conduit to force away gas already present in the reservoir.

2. The arrangement according to claim 1, wherein the reservoir encloses an inner space having a lower part, configured to receive the blood from the cardiotomy, and an upper part, configured to receive gas from the cardiotomy, and wherein supply device is configured to supply the displacing gas to the reservoir to force away said gas already present in the upper part.

3. The arrangement according to claim 2, wherein the reservoir comprises an outlet opening permitting the upper part of the inner space of the reservoir to communicate with the surrounding atmosphere to release said gas already present from the upper part.

4. The arrangement according to claim 2, wherein the supply conduit comprises an outlet member provided in the inner space of the reservoir.

5. The arrangement according to claim 4, wherein the outlet member is provided in the upper part of the inner space.

6. The arrangement according to claim 4, wherein the outlet member extends into the lower part of the inner space.

7. The arrangement according to claim 1, wherein the supply conduit comprises a filter for filtering the displacing gas before entering the reservoir.

8. The arrangement according to claim 1, wherein the supply conduit comprises a control valve configured to permit control of the flow of the displacing gas to the reservoir.

9. The arrangement according to claim 1, wherein the supply device comprises a humidifying device configured to humidify the displacing gas to be supplied to the reservoir via the supply conduit.

10. The arrangement according to claim 1, wherein the arrangement comprises a venous connection configured to be connected to venous blood of a patient, and wherein the reservoir is connected to the venous connection and configured to receive the blood from the venous connection.

11. The arrangement according to claim 1, wherein the reservoir comprises a cardiotomy reservoir, and wherein the arrangement comprises a venous connection configured to be connected to venous blood of a patient, and a venous reservoir connected to the venous connection and configured to receive the blood from the venous connection.

12. The arrangement according to claim 9, wherein the venous reservoir and the cardiotomy reservoir are included in a common container.

13. The arrangement according to claim 1, wherein the arrangement comprises a further supply device configured to supply carbon dioxide to the cardiotomy of the patient.

14. A method for cardiopulmonary bypass, comprising the steps of:
   conveying blood from the cardiotomy of a patient to a reservoir;
   supplying the blood from the reservoir to an oxygenator;
   filtering the blood from the oxygenator;
   supplying the filtered blood to the patient and supplying a displacing gas to the reservoir.

15. The method according to claim 14, comprising the step of supplying the displacing gas to an inner space of the reservoir to force away gas already present in an upper part of the inner space, wherein the blood from the is received in a lower part of the inner space of the reservoir.

16. The method according to claim 15, comprising the step of:
   releasing said gas already present from the upper part of the inner space of the reservoir through an outlet opening permitting the upper part of the inner space of the reservoir to communicate with the surrounding atmosphere.

17. The method according to claim 16, comprising the step of:
   supplying the displacing gas in a laminar flow in the upper part of the inner space of the reservoir.

* * * * *